US005360715A

United States Patent [19]

Leavitt et al.

[11] Patent Number: 5,360,715

[45] Date of Patent: Nov. 1, 1994

[54] PLASTIN ISOFORMS AND THEIR USES

[75] Inventors: John C. Leavitt, Palo Alto; Ching-Shwun Lin, Redwood City, both of Calif.; Ruedi H. Aebersold, Vancouver, Canada

[73] Assignee: California Institute of Technology, Pasadena, Calif.

[21] Appl. No.: 642,983

[22] Filed: Jan. 10, 1991

Related U.S. Application Data

[60] Division of Ser. No. 495,256, Mar. 16, 1990, Pat. No. 5,002,870, which is a continuation-in-part of Ser. No. 203,434, Jun. 7, 1988, abandoned.

[51] Int. Cl.$^5$ ........................ C12Q 1/68; C07H 21/04; C07K 13/00; G01N 33/53

[52] U.S. Cl. ........................................ 435/6; 435/7.8; 536/23.5; 536/24.3; 536/24.31; 530/324; 530/350; 530/380

[58] Field of Search ...................... 536/27, 23.5, 24.3, 536/24.31; 435/6, 7.8; 530/324, 350, 380

[56] References Cited

PUBLICATIONS

Lin et al. (1988, Nov.) Molecular and Cellular Biology, pp. 4659–4668, vol. 8(11).
Aebersold et al. (1987) Proceeding National Acad. Sci., vol. 84, pp. 6970–6974.
Sanger et al., vol. 74, (1977), P.N.A.S. pp. 5463–5467.
Varma, Exp. Cell Res (1987) 173:163–173.
Leavitt, et al, *Cell* 28:259–268 (1982).
Goldstein, et al, *Cancer Res.* 45:3256–3261 (1985).
Leavitt, et al, *Mol. Cell. Biol.* 6:2721–2726 (1986).
Leavitt, et al, *J. Biol. Chem.* 255:1650–1661 (1980).
Leavitt, et al, *Carcinogenesis* (*London*) 3:61–70 (1982).
Goldstein, et al, *Cancer Res.* 45:5643–5647 (1985).
Goldman, et al, *Clin. Chem.* 28:1021–1025 (1982).
Goldman, et al, *Am. J. Hum. Genet.* 35:827–837 (1983).
Goldman, et al, *Am. J. Hum. Genet.* 37:898–911 (1985).
Kondo, et al, *Am. J. Hum. Genet.* 37:1106–1111 (1985).

*Primary Examiner*—Mindy B. Fleisher
*Attorney, Agent, or Firm*—Skjerven, Morrill, MacPherson, Franklin & Friel

[57] ABSTRACT

A method and reagents are provided for determining whether a human cell is a hemopoietic cell and whether a human tissue cell is in a neoplastic state. Human cells which express only leukocyte-plastin (l-plastin) are hemopoietic cells and human cells which express both l-plastin and tissue-plastin (t-plastin) are neoplastic. The method can be performed using isoform-specific plastin nucleotide probes or isoform-specific anti-plastin antibodies.

16 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1: Table 2, pages 18-20

( i ) SEQUENCE CHARACTERISTICS:
( A ) LENGTH: 1713 nucleotides/570 amino acids
( B ) TYPE: nucleic acid and amino acids encoded thereby
( C ) STRANDEDNESS: cDNA (corresponding to double stranded DNA)
( D ) TOPOLOGY: linear ( i i ) MOLECULE TYPE:
( A ) DESCRIPTION: cDNA and encoded protein ( i i i ) HYPOTHETICAL: No ( i v ) ANTI-SENSE: No ( v ) FRAGMENT TYPE: 3'coding sequence/C-terminal fragment ( v i ) ORIGINAL SOURCE:
( A ) ORGANISM: homo sapiens
( D ) DEVELOPMENTAL STAGE: adult cells
( F ) TISSUE TYPE: blood cells
( G ) CELL TYPE: lymphoblastoid
( H ) CELL LINE: CEM lymphoblastoid cells
( I ) ORGANELLE: total cell lysate ( v i i ) IMMEDIATE SOURCE:
( A ) LIBRARY: HuT-14 cDNA library (human fibrosarcoma cDNA library)
( B ) CLONE: P4 (T-plastin), P107 (L- plastin)

( v i i i ) POSITION IN GENOME:
( A ) CHROMOSOME/SEGMENT: chromosome 13 ( L - p l a s t i n )/chromosome X (T-plastin)

-continued ( i x ) FEATURES:
( A ) NAME/KEY: cDNA and encoded protein
( B ) LOCATION: nt 1-1713/aa 1-570
( C ) IDENTIFICATION METHOD: peptides corresponding to protein were sequenced and used to prepare nucleotide probes ( x ) PUBLICATION INFORMATION:
( A ) AUTHORS: Lin, Aebersold, Kent, Varma, Leavitt
( B ) TITLE: Molecular Cloning and Characterization of Plastin, a Human Leukocyte Protein Expressed in Transformed Human Fibroblasts
( C ) JOURNAL: Molec. Cell. Biol.
( D ) VOLUME: 8
( E ) ISSUE: 11
( F ) PAGES: 4659-4668
( J ) PUBLICATION DATE: November, 1988
( K ) RELEVANT RESIDUES IN SEQ ID NO: 1: All ( x i ) SEQUENCE DESCRIPTION: SEQ ID NO: 1:

( 2 ) INFORMATION FOR SEQ ID NO: 2:

( i ) SEQUENCE CHARACTERISTICS:
( A ) LENGTH: 1713 nucleotides/570 amino acids
( B ) TYPE: nucleic acid and amino acids encoded thereby
( C ) STRANDEDNESS: cDNA (corresponding to double stranded DNA)
( D ) TOPOLOGY: linear ( i i ) MOLECULE TYPE:
( A ) DESCRIPTION: cDNA and encoded protein ( i i i ) HYPOTHETICAL: No ( i v ) ANTI-SENSE: No ( v ) FRAGMENT TYPE: 5'coding sequence/N-terminal fragment ( v i ) ORIGINAL SOURCE:
( A ) ORGANISM: homo sapiens
( D ) DEVELOPMENTAL STAGE: adult cells
( F ) TISSUE TYPE: blood cells
( G ) CELL TYPE: lymphoblastoid
( H ) CELL LINE: CEM lymphoblastoid cells
( I ) ORGANELLE: total cell lysate ( v i i ) IMMEDIATE SOURCE:
( A ) LIBRARY: HuT-14 cDNA library (human fibrosarcoma cDNA library)
( B ) CLONE: P4 (T-plastin), P107 (L- plastin)

( v i i i ) POSITION IN GENOME:
( A ) CHROMOSOME/SEGMENT: chromosome 13 ( L - p l a s t i n )/chromosome X (T-plastin)

( i x ) FEATURES:
( A ) NAME/KEY: cDNA and encoded protein
( B ) LOCATION: nt 1-1713/aa 1-570
( C ) IDENTIFICATION METHOD: Amplified from mRNA ( x ) PUBLICATION INFORMATION:
( A ) AUTHORS: Lin, Aebersol, Leavitt
( B ) TITLE: Correction of the N- Terminal Sequences of the Human Plastin Isoforms by Using Anchored Polymerase Chain Reaction: Identification of a Potential Calcium-Binding Comain
( C ) JOURNAL: Molec. Cell. Biol.
( D ) VOLUME: 10
( E ) ISSUE: 4
( F ) PAGES: 1818-1821
( G ) DATE: submitted 10/31/89

-continued ( J ) PUBLICATION DATE: April, 1990
( K ) RELEVANT RESIDUES IN SEQ ID NO: 1: All ( x i ) SEQUENCE DESCRIPTION: SEQ ID NO: 2:

PLASTIN ISOFORMS AND THEIR USES

CROSS REFERENCE TO RELATED APPLICATION

The present application is a Division of U.S. application Ser. No. 07/495,256 filed Mar. 16, 1990, now U.S. Pat. No. 5,002,870 which application is a continuation-in-part application of U.S. application Serial No. 07/203,434 filed Jun. 7, 1988 now abandoned entitled Plastin Isoforms and Their Uses by John C. Leavitt, Ching-Shwun Lin and Ruedi H. Aebersold, which application is incorporated herein by reference in its entirety.

FIELD OF THE INVENTION

The present invention relates to methods for characterizing cells and, in particular, to methods for determining whether a human cell is a hemopoietic cell and whether a human tissue cell is neoplastic.

BACKGROUND OF THE INVENTION

The importance of oncogenes in the development of human cancer has been amply demonstrated in recent years by the ability of these genes to cause tumorigenic conversion of rodent cells. There can be no doubt that other human genes exist which are not classified as oncogenes per se but which play important roles in the development and progression of cancer. One category of these genes encodes abundant structural proteins such as the actins and tropomyosins. The involvement of these abundant proteins in the neoplastic transformation process is suggested by the well documented observations that isoforms within these structural protein families are consistently modulated in transformation of avian, rodent and human cells. This second category of cancer-related genes is set apart from the so-called "oncogenes" because modulation of these genes in a transformation-sensitive manner is likely to result from regulatory processes activating transcription or translation rather than by direct activation through mutational processes.

An abundant phosphorylated polypeptide, plastin is frequently expressed in human cancer cells of solid tissue but is not expressed in normal human fibroblasts. The same protein was one of the most abundant constitutively expressed proteins of human white blood cells. Thus, plastin may be associated with transformation of non-hemopoietic cells. Despite the reproducible identification of plastin and studies of its expression and polymorphic character, nothing was known of its molecular identity.

RELEVANT LITERATURE

The abundant proteins synthesized in normal and transformed human fibroblasts were examined by means of comparative high resolution two-dimensional polyacrylamide gel electrophoresis. An abundant phosphorylated polypeptide plastin ($M_r$ 68,000, pI 5.3) that is frequently expressed in human cancer cells of solid tissue but that is not expressed in normal human fibroblasts was identified (Leavitt et al, Cell (1982) 28:259–268; Goldstein et al, *Cancer Res.* (1985a) 45:3256–3261; Leavitt et al, *Mol. Cell. Biol.* (1986) 6:2721–2726; Leavitt et al, *J. Biol. Chem.* (1980) 255:1650–1661; Leavitt et al, *Carcinogenesis* (London) (1982) 3:61–70). When proteins of normal peripheral blood leukocytes were examined, the same protein was one of the most abundant constitutively expressed proteins of white blood cells (Goldstein et al, *Cancer Res.* (1985b) 45:5643–5647). Cross-identification of plastin in the transformed fibroblasts and leukocytes was based upon the finding that the protein identified as plastin in mixed proteins of the two cell types comigrated in a two-dimensional gel as a single spot. Furthermore, two separate peptide antibodies specific for the amino acid sequence around residue 244 of actin cross-reacted with plastin from either transformed fibroblasts or lymphocytes in a two-dimensional (2-D) gel western blot (Varma et al, *Exp. Cell. Res.* (1987) 173:163–173).

Goldman, Merril and colleagues (Goldman et al, *Clin. Chem.* (1982) 28:1021–1025) observed that plastin was polymorphic in charge among 28 individuals whose leukocyte proteins were examined by 2-D gel electrophoresis. They later referred to this protein as NIMH4 and NC4 (Goldman et al, *Am. J. Hum. Genet.* (1983) 35:827–837; Goldman et al, *Am. J. Hum. Genet.* (1985) 37:898–911). NIMH4 (or NC4) and l-plastin of fibroblasts were determined to be the same polypeptide (Leavitt et al (1982), supra). Later, Goldstein et al also reported that l-plastin was polymorphic in human leukocytes (Goldstein et al (1985b), supra). Independently, Kondo and Hamaguchi (Kondo et al, *Am. J. Hum. Genet.* (1986) 37:1106–1111) used the polymorphic character of plastin (LCPl, NIMH4, NC4, or p219/p220) in a gene segregation analysis to link the l-plastin gene to the esterase D and retinoblastoma locus on human chromosome 13.

SUMMARY OF THE INVENTION

A method and reagents are provided for determining whether a human cell is a hemopoietic cell and whether a human tissue cell is in a neoplastic state. Human cells which express only leukocyte-plastin (l-plastin) are hemopoietic cells and human cells which express both l-plastin and tissue-plastin (t-plastin) are neoplastic. The method can be performed using isoform-specific plastin nucleotide probes or isoform-specific anti-plastin antibodies.

DESCRIPTION OF THE SPECIFIC EMBODIMENTS

A method for distinguishing human hemopoietic cells, normal human tissue cells and neoplastic human tissue cells is provided. The method is based on the observation that there are two isoforms of plastin, leukocyte-plastin (l-plastin) and tissue-plastin (t-plastin). Tissue cells express t-plastin, while neoplastic tissue cells additionally express l-plastin. Hemopoietic cells express l-plastin, but neither neoplastic nor normal hemopoietic cells express t-plastin. Therefore a cell that expresses t-plastin is a tissue cell; a cell that expresses only l-plastin is a hemopoietic cell; and a cell that expresses both t-plastin and l-plastin is a neoplastic tissue cell. Isoform-specific nucleic acid probes and isoform-specific anti-plastin antibodies are also provided.

It has now been found that the two isoforms of plastin, t-plastin and l-plastin, have approximately 80% of their amino acids in common and the genes encoding the isoforms have about 60% of their nucleotides in common. The l-plastin isoform is polymorphic. There are at least two species of the t-plastin isoform, which differ by charge. It has not been determined whether these species are encoded by different genes or are encoded by the same gene and differ as the result of post-translational processing. However, a full-length DNA sequence encoding t-plastin hybridizes with mRNA producing each of the t-plastin species under stringent hybridization conditions. Therefore, although the two species of t-plastin may actually be different isoforms of the protein, they will be referred to as the t-plastin isoform for purposes of this application, since each is distinguishable from the l-plastin isoform using the same nucleotide probe or antibody composition.

A DNA fragment of at least about 1700 bp and fewer than about 50 kbp, usually fewer than 30 kbp, comprising a DNA sequence encoding a human plastin isoform or the 5' and 3' flanking non-coding regions is provided. The fragment may be a cDNA sequence comprising the coding and adjacent transcribed regions, usually of not more than about 5 kbp, or a genomic sequence including non-transcribed regions of the gene. The isolation of cDNA sequences and genomic DNA sequences encoding l-plastin and t-plastin is described in detail in the Experimental section. Table 2 in the Experimental section provides the complete nucleotide sequences and the deduced amino acid sequences of cDNA fragments encoding t-plastin and l-plastin isolated from a λgtlO cDNA library of transformed human fibroblasts.

These fragments containing the full-length coding sequence of 627 to 630 amino acids (Tables 2 and 3) find use as probes for detecting human plastin-encoding genes or closely-related genes in human or other species and for detecting mRNA expressing human plastin. The fragments may also be used to express the encoded plastin isoform by preparing by conventional means an expression construct containing the fragment under the transcriptional and translational control of a promoter. The promoter may be a eukaryotic promoter for expression in a mammalian cell. In cases where one wishes to expand the promoter or produce the peptide isoforms or fragments thereof in a prokaryotic host, the promoter may also be a prokaryotic promoter. Usually a strong promoter will be employed for high level transcription and expression.

The expression construct may be part of a vector capable of stable extrachromosomal maintenance in an appropriate cellular host or may be integrated into host genomes. Normally, markers are provided with the expression construct which allow for selection of a host containing the construct. The marker may be on the same or a different DNA molecule, desirably, the same DNA molecule.

The expression construct can be joined to a replication system recognized by the intended host cell. Various replication systems include vital replication systems such as retroviruses, simian virus, bovine papilloma virus, or the like. In addition, the construct may be joined to an amplifiable gene, e.g. DHFR gene, so that multiple copies of the fragment may be made. Introduction of the construct into the host will vary depending on the construct and can be achieved by any convenient means. A wide variety of hosts may be employed for expression of the peptides, both prokaryotic and eukaryotic.

Nucleotide sequences of at least about 20 nucleotides and not more than about 50 kbp, usually less than 30 kbp, which include at least about 20 consecutive nucleotides complementary to a DNA sequence encoding a plastin isoform or the adjacent non-coding regions also find use as probes. Usually the nucleotides will be complementary to the transcribed portions of the plastin gene, desirably the coding region; however, the untranscribed regions find use in isolating genomic sequences. Usually the probe will have at least about 50, more usually about 100, generally 500 nt complementary nucleotides. Desirably, when using probes of less than about 500 nt, the probe will share not more than about 60% homology with a DNA sequence encoding the other plastin isoform, usually not more than about 50% homology. In a preferred embodiment, the probe will be complementary to at least a portion of a DNA sequence encoding the N-terminal 24 amino acids (amino acids 1 through 24 and amino acids 58 through 82; Table 3), usually the N-terminal 19 amino acids of the plastin isoform (amino acids 1 through 19 and amino acids 58 through 77; Table 3). Desirably, the probe will include a sequence encoding the N-terminal 20 amino acids of the plastin isoform. In a preferred embodiment, the probe will include an oligonucleotide sequence in Tables 2 and 3. The probes may be used to detect genes encoding plastin or to express at least a portion of the plastin isoform. Usually, however, the probe will be a DNA sequence which finds use to determine whether a cell produces mRNA expressing the isoform.

A substantially pure composition of a plastin isoform may be produced by expressing a DNA fragment of this invention. Peptides corresponding to a portion of the plastin isoform peptide sequence can be produced by recombinant technology or can be chemically synthesized. In a preferred embodiment, a peptide of less than about 100 amino acids comprises at least about 10 consecutive amino acids, more usually at least 15 consecutive amino acids, from the amino acid sequence of a plastin isoform or sequences immunologically cross-reactive therewith. Desirably, the peptide will have at least about 5 consecutive amino acids, usually 10, more usually 15, of the N-terminal about 15 to about 20 amino acids of the plastin isoform sequence. Peptides of less than about 50 amino acids, more usually less than about 30 amino acids, and comprising about 15 to about 20 amino acids of the N-terminal sequence or amino acids 58 through 82 of the plastin isoform may find use to induce isoform-specific anti-plastin antibodies. In a preferred embodiment, the peptide sequence includes at least about 10 consecutive amino acids from the sequence MLDGDRNKDGKISFDEFVYI, (from Table 2), MATGDLDQDGRISFDEFIKI (from Table 2), MDEMATTQISKDELDELKEA (from Table 3), or MARGSVSDEEMMELREAFAK (from Table 3).

The peptides may also be used to quantify a peptide isoform as controls or as analyte analogue in competitive inhibition analyses, to determine the specificity of an antibody composition or to purify an antibody composition.

Desirably, peptides used for production of isoform-specific antibodies will share not more than about 60% homology, usually not more than about 50% homology, desirably 40% homology or less, with the other plastin isoform. The first 15 to 20 amino acids of the N-terminus of plastin isoforms share fewer common amino acids than many other portions of the isoform sequence of the same length. Thus, the N-terminal sequence of the isoform is conveniently included in the peptides. However, the whole plastin polypeptide can be used to produce monoclonal antibodies which are isoform-specific to any sequence on the plastin polypeptide chain which differs between isoforms.

An isoform-specific anti-plastin antibody composition reacts with a plastin isoform and exhibits substantially no reaction with the other plastin isoform. The antibody composition desirably has an affinity for the isoform suitable for detection of the isoform on a solid substrate, particularly a Western blot, and exhibits only a background level of binding with the other isoform. The antibody affinity required for detection of a plastin isoform using a particular immunoassay method will not differ from that required to detect other polypeptide analytes. The antibody composition may be polyclonal or monoclonal, desirably monoclonal.

Isoform-specific antibodies can be produced by a number of methods. Polyclonal antibodies may be induced by administering an immunogenic composition comprising a peptide of this invention to a host animal. Preparation of immunogenic compositions may vary depending on the host animal and is well known. For example, the peptide may be conjugated to an immunogenic substance such as KLH or BSA or provided in an adjuvant or the like. The induced antibodies can be tested to determine whether the composition is isotype-specific. If a polyclonal antibody composition does not provide the desired specificity, the antibodies can be purified to provide an isoform-specific composition by a variety of conventional methods. For example, when one isoform is used to induce antibodies, the composition can be contacted with the other isoform affixed to a solid substrate to remove those antibodies which bind to the other isoform. Either prior to or following that purification, if desired, the composition can be purified to reduce binding to other substances by contacting the composition with the desired isoform affixed to a solid substrate. Those antibodies which bind to the desired isoform are retained. Purification techniques using peptides or antibodies affixed to a variety of solid substrates such as affinity chromatography materials including Sephadex, Sepharose and the like are well known.

Monoclonal isoform-specific anti-plastin antibodies may also be prepared by conventional methods. A mouse can be injected with an immunogenic composition comprising a peptide or whole plastin polypeptide of this invention and spleen cells obtained. Those spleen cells can be fused with a fusion partner to prepare hybridomas. Antibodies secreted by the hybridomas can be screened to select a hybridoma wherein the antibodies react with one plastin isoform and exhibit substantially no reaction with the other plastin isoform. Hybridomas that produce antibodies of the desired specificity are cultured by standard techniques. Hybridoma preparation techniques and culture methods are well known and constitute no part of the present invention.

Exemplary preparations of monoclonal and polyclonal antibodies are described in the examples.

A method of determining whether a cell is hemopoietic comprises determining whether l-plastin, but not t-plastin, is present in the cell. Cells that have l-plastin but not t-plastin are hemopoietic. Prior to the present invention cells could be determined to be hemopoietic by a variety of means. For example, cells can be determined to be hemopoietic histologically or by detecting the presence of a variety of markers specific for different types of hemopoietic cells. The present technique is particularly advantageous in that a marker common to a plurality of types including all stem cells of hemopoietic cells had not previously been found. As described in detail in the Experimental section, it has now been determined that all cells of hemopoietic origin except fully differentiated red blood cells and platelets, exhibit abundant synthesis of l-plastin, and fail to express t-plastin. Therefore, l-plastin is a marker common to all cells of hemopoietic origin that replicate. Further, all cells that express l-plastin but fail to express t-plastin are hemopoietic cells.

A method for determining whether a tissue cell is in a neoplastic state comprises determining whether l-plastin is present in the cell. Tissue cells which express l-plastin are neoplastic. Although the cell can be determined to be a non-hemopoietic cell by any of a number of methods, conveniently, the cell will be determined to be a tissue cell by detecting the presence of t-plastin. A cell which expresses both t- and l-plastin is a neoplastic tissue cell. Of course, if a cell expresses only t-plastin or only l-plastin, the cell may be neoplastic. That is, a positive result (presence of both t- and l-plastin) indicates that a cell is neoplastic, but a negative result is not conclusive.

To determine whether a cell expresses l- and/or t-plastin, an isoform-specific plastin probe or an isoform-specific anti-plastin antibody can be used to detect the presence of mRNA or plastin peptide isoform, respectively. When using a probe, the probe will be hybridized to mRNA from the cell under stringent hybridization conditions. An exemplary method of detecting mRNA encoding a plastin isoform by a Northern blot analysis is described in the Experimental section.

Detecting mRNA is conveniently performed on a cell which has been cultured to provide a number of identical cells sufficient for mRNA analysis. However, in neoplastic tissue cells, the amount of l-plastin mRNA present in a cell comprises about 0.1% to about 200% of the amount of t-plastin mRNA. Therefore, the sample being analyzed has been determined to contain only a small percentage of hemopoietic cells, desirably less than 0.001% by weight, the presence of l-plastin mRNA in a substantial percentage of the tissue cells, usually at least about 0.1%, desirably 1.0% or more, can be distinguished from l-plastin mRNA in the contaminating hemopoietic cells.

Alternatively, the presence of t- or l-plastin can be detected using isoform-specific anti-plastin antibodies. A variety of methods of detecting polypeptides with specific antibodies are well known. Since plastin comprises a major component of the cell cytosol, determination of which isoforms are present in particular cells is conveniently performed by preparing the cells for staining by standard histologic techniques such as embedding formalin-fixed cells in paraffin. The isoform-specific antibodies can be conjugated to distinguishable labels, such as rhodamine and fluorescein, and used simultaneously to stain the cells. Flowcytometry with a fluorescence-activated cell sorter may also be used to identify single cells that express both plastin isoforms. Such methods unambiguously indicate the presence of both isoforms within a cell.

However, similar techniques may be sufficient in particular circumstances. For example, samples could be sequentially stained with each of the isoform-specific antibodies. When a statistically larger percentage of cells stain with anti-l-plastin than do not stain with anti-t-plastin, there are cells in the sample that contain both l- and t-plastin. That or similar methods may also find use with samples substantially free from hemopoietic cells or samples having a significant percentage of neoplastic cells.

Additionally, quantitative measurements of plastin isoforms in various bodily fluids such as serum and human milk may be indicative of disease states. For example, elevated levels of l-plastin in serum may be indicative of lyric infections of lymphocytes present in diseases such as AIDS. A preferred assay is a Western blot which definitively demonstrates that the correct peptide has been detected through the combination of the use of gel electrophoresis and immunoassay analysis. However, other immunoassay methods may also find use. Numerous quantitative immunoassay methods for detecting a peptide in a bodily fluid are known. An assay method has the following elements. The method comprises combining the sample with the isoform-specific antibody and detecting the presence of isoform-specific antibody-peptide complex as indicative of the presence of the peptide in the sample. The particular manner in which the peptide is detected is not significant for the purpose of this invention so long as the method provides the desired degree of sensitivity and reliability.

A number of different types of immunoassays are well known using a variety of protocols and labels. The assay conditions and reagents may be any of a variety found in the prior art. The assay may be heterogeneous or homogeneous, usually heterogeneous, conveniently a sandwich assay.

The assay will usually employ solid phase-affixed isoform-specific anti-plastin antibodies. The antibodies may be polyclonal or monoclonal, usually monoclonal. The solid phase-affixed antibodies are combined with the sample. Binding between the antibodies and sample can be determined in a number of ways. Complex formation can be determined by use of soluble antibodies specific for the isoform to be detected. The antibodies can be labeled directly or can be detected using labeled second antibodies specific for the species of the soluble antibodies. Various labels include radionuclides, enzymes, fluorescers or the like. Conveniently, the assay will be an enzyme-linked immunosorbent assay (ELISA) in which monoclonal antibodies specific for different epitopes of the plastin isoform are used as the solid phase-affixed and enzyme-labeled, soluble antibodies.

Alternatively, the assay may be based on competitive inhibition, where plastin in the sample competes with a known amount of a plastin isoform for a predetermined amount of isoform-specific anti-plastin antibody. For example, any of the plastin isoform present in the sample can compete with a known amount of the labeled plastin isoform or isoform analogue for antibody binding sites. The amount of labeled isoform affixed to the solid phase or remaining in solution can be determined.

The following examples are offered by way of illustration and not by way of limitation.

EXPERIMENTAL

EXAMPLE 1

Isolation and Sequencing of cDNA Encoding Plastin Isoforms

Two isolation techniques which were developed for protein microsequencing (Aebersold et al, *J. Biol. Chem.* (1986) 261:4229-4238; Aebersold et al, *Methods in protein sequence analysis*, K. Walsh, ed., Human Press, Clifton, N.J. (1987a), p. 277-294; Aebersold et al, *Proc. Natl. Acad. Sci. USA* (1987b) 84:6970-6974) were used to obtain sequence information from plastin purified from two-dimensional gels. For N-terminal sequence analysis, proteins were electroblotted from analytical two-dimensional gels onto chemically-modified glass fiber filter paper and detected by fluorescent staining. Plastin spots were cut out and inserted into the sequenator cartridge for direct sequence analysis (Aebersold et al (1986), supra; Aebersold et al (1987a), supra). The amino acid sequence analysis was performed on an automated Caltech gas-phase sequenator (Hewick et al, *J. Biol. Chem.* (1981) 256:7990-7997).

In repeated attempts, an N-terminal sequence from T-lymphocyte plastin was not obtained, although proteins expressed at comparable levels and simultaneously isolated from the same two-dimensional gels were readily sequenced (Aebersold et al (1987a), supra). This suggested that plastin was blocked at the amino terminal end. Using a newly-developed procedure (Aebersold et al (1987b), supra), internal protein sequence information of plastin was obtained.

Proteins in a total cell lysate of CEM lymphoblastoid cells were separated by two-dimensional gel electrophoresis and electroblotted onto nitrocellulose. Plastin containing spots were excised and enzymatically cleaved on the nitrocellulose matrix (Aebersold et al (1987b), supra). The resulting peptides were separated by narrow-bore reversed-phase HPLC and individual peptide fragments were sequenced in a modified Caltech gas-phase sequenator (Kent et al, *Biotech.* (1987) 5:314-321). Four peptide sequences that were unambiguously identified are listed in Table 1.

TABLE 1

(A) Four Unambiguous Plastin Peptide Sequences

. . .Glu—Val—Ile—Pro—Met—Asn—Pro—Asn—Ser/or Thr—Asn—Asp—blank—Phe—blank—Ala—Val. . .

. . .Thr—Ile—Gln—Glu—Asn—Leu—Asn—Leu—Ala—Leu—Asn—Ser—Ala—Ser—Blank—Ile—Gly. . .

. . .Val—Asn—Asp—Asp—Ile—Ile—Val—Asn—Tyr—Val—Asn—Glu. . .

. . .Ile—Ser—Thr—Ser—Leu—blank—Val—Leu—Asp—Leu—Ile—Asp. . .

(B) Synthesis of a Degenerate Oligonucleotide Probe for Plastin

| Amino Acid Position | Oligopeptide Sequence | Oligonucleotide Probe (Antisense) | Corresponding l-Plastin Nucleotide Sequence (Sense) |
|---|---|---|---|
| | | 3′ end | |
| 1 | Val | C | G |
| | | A | T |
| | | CG | C |
| 2 | Asn | T | A |
| | | T | A |
| | | AG | T |
| 3 | Asp | C | G |
| | | T | A |

TABLE 1-continued

| | | | |
|---|---|---|---|
| | | AG | T |
| 4 | Asp | C | G |
| | | T | A |
| | | AG | C |
| 5 | Ile | T | A |
| | | A | T |
| | | I | T |
| 6 | Ile | T | A |
| | | A | T |
| | | I | T |
| 7 | Val | C | G |
| | | A | T |

A degenerate oligonucleotide 20-mer corresponding to one of the four oligopeptides (shown in Table 1) was synthesized and used to screen a λgtlO cDNA library of transformed (HuT-14) human fibroblasts (Lin et al, *J. Mol. Cell. Biol.* (1988) 8:160–168). From approximately 10,000 recombinants, the probe selected a single clone, P4.

Cellular RNAs were prepared by the guanidine hydrochloride method (as previously described in Gunning et al, *J. Mol. Evol.* (1984) 20:202–214). Five microgram of each RNA was electrophoresed in a 1% agarose gel containing 50 mM morpholinepropanesulfonic acid (pH 7), 1 mM EDTA, and 2.2M formaldehyde; blotted onto nitrocellulose; and hybridized with nick-translated probes (Rigby et al, *J. Mol. Biol.* (1977) 113:237–251). Hybridization proceeded overnight at 65° C. in 4x SSC (1x SSC is 150 mM NaCl and 15 mM sodium citrate, pH 7), 5x Denhardt's solution (Denhardt, *Biochem. Biophys. Res. Comm.* (1966) 23:641–646), 50 mM phosphate buffer (pH 7), 10% (w/v) dextran sulfate, and 2×106 cpm/ml probe. Washing was carried out twice in 1x SSC and 0.1% (w/v) sodium dodecyl sulfate (SDS) at room temperature for 5 min. each, and twice in 0.5x SSC and 0.1% SDS at 65° C. for 30 min each. Two identical Northern blots were hybridized using Northern analysis with 32P-labeled cDNAs of P4 and P107, respectively. Each blot contained cellular RNAs of CEM, KD, and HuT-14. Size markers were 28S and 18S ribosomal RNAs (5 kb [kilobases] and 2 kb, respectively).

The cDNA insert of P4 was 4.3 kb in length. (This large cDNA was later determined to be comprised of two unrelated cDNA fragments of 1.0 kb and 3.3 kb that were ligated during the construction of the library.) A 2 kb HindIII fragment within the 3.3 kb cDNA insert of P4 hybridized to an mRNA of 3.4 kb that was more abundant in HuT-14 than in normal KD fibroblasts and not detectable in CEM T-lymphocytes.

cDNA was cloned into M13mp9 (Messing, *J. Methods in Enzymol.* (1983) 101: 20–78). Progressive deletion clones were prepared by the method described by Dale et al, Plasmid (1985) 13:31–40. Sequencing was done by the method described by Sanger et al, *Proc. Natl. Acad. Sci. USA* (1977) 74:5463–5467. Table 2 illustrates the coding sequences and deduced amino acid sequences of P4 cDNA (top, t-plastin) and P107 cDNA (bottom, l-plastin). Identical nucleotides between the two sequences are indicated by double dots. As shown in the table, the cDNA sequences share about 60% homology, while the peptide sequences share about 80% homology.

TABLE 2

```
         M  L  D  G  D  R  N  K  D  G  K  I  S  F  D  E  F  V  Y  I  F  Q  E   23
P4 ->   ATGCTGGATGGTGACAGGAATAAAGATGGGAAAATAAGTTTTGACGAATTTGTTTATATTTTTCAAGAG
        :::      :::::   : :  ::::::: :  :: :: ::::: :: ::: :  : ::::: :: :  
P107 -> ATGGCTACAGGTGATCTGGACCAAGATGGAAGGATCAGCTTTGATGAGTTTATCAAGATTTTCCATGGC
         M  A  T  G  D  L  D  Q  D  G  R  I  S  F  D  E  F  I  K  I  F  H  G

         V  K  S  S  D  I  A  K  T  F  R  K  A  I  N  R  K  E  G  I  C  A  L   46
        GTAAAAAGTAGTGATATTGCCAAGACCTTCCGCAAAGCAATCAACAGGAAAGAAGGTATTTGTGCTCTG
         ::::::: :  ::: :::::::::::::  : ::::::::::: : ::: ::::: ::::::::  : 
        CTAAAAAGCACAGATGTTGCCAAGACCTTTAGAAAAGCAATCAATAAGAAGGAAGGGATTTGTGCAATC
         L  K  S  T  D  V  A  K  T  F  R  K  A  I  N  K  K  E  G  I  C  A  I

         G  G  T  S  E  L  S  S  E  G  T  Q  H  S  Y  S  E  E  E  K  Y  A  F   69
        GGTGGAACTTCAGAGTTGTCCAGCGAAGGAACACAGCATTCTTACTCAGAGGAAGAAAAATATGCTTTT
        ::::: :::::::::  ::: ::::  :: :: :: :: :: :: :::::::::::::: ::::: :::
        GGTGGTACTTCAGAGCAGTCTAGCGTTGGCACCCAACACTCCTATTCAGAGGAAGAAAAGTATGCCTTT
         G  G  T  S  E  Q  S  S  V  G  T  Q  H  S  Y  S  E  E  E  K  Y  A  F

         V  N  W  I  N  K  A  L  E  N  D  P  D  C  R  H  V  I  P  M  N  P  N   92
        GTTAACTGGATAAACAAAGCTTTGGAAAATGATCCTGATTGTAGACATGTTATACCAATGAACCCTAAC
        :: :::::::::::::::::  :::::::::::::::::::: : ::::: :: ::::::::::: :::
        GTCAACTGGATAAACAAAGCCCTGGAAAATGATCCTGATTGTCGGCATGTCATCCCAATGAACCCAAAC
         V  N  W  I  N  K  A  L  E  N  D  P  D  C  R  H  V  I  P  M  N  P  N
                                         peptide #1 -> E  V  I  P  M  N  P  N

         T  D  D  L  F  K  A  V  G  D  G  I  V  L  C  K  M  I  N  L  S  V  P   115
        ACCGATGACCTGTTCAAAGCTGTTGGTGATGGAATTGTGCTTTGTAAAATGATTAACCTTTCAGTTCCT
        ::  :::: :: :: :: :::::::: ::::: ::::: :::::::::::::: ::::: ::::: :: 
        ACGAATGATCTCTTTAATGCTGTTGGAGATGGCATTGTCCTTTGTAAAATGATCAACCTGTCAGTGCCA
         T  N  D  L  F  N  A  V  G  D  G  I  V  L  C  K  M  I  N  L  S  V  P
        S/T N  D  -  F  -  A  V

         D  T  I  D  E  R  A  I  N  K  K  K  L  T  P  F  I  I  Q  E  N  L  N   138
        GATACCATTGATGAAAGAGCAATCAACAAGAAGAAACTTACACCCTTCATCATTCAGGAAAACTTGAAC
        :: :: :::::::::::: :::::::::: ::::: :: :: :: :::: ::::::::::::  :::::
        GACACAATTGATGAAAGAACAATCAACAAAAAGAAGCTAACCCCTTTCACCATTCAGGAAAATCTGAAC
         D  T  I  D  E  R  T  I  N  K  K  K  L  T  P  F  T  I  Q  E  N  L  N
                                            peptide #2 -> T  I  Q  E  N  L  N

         L  A  L  N  S  A  S  A  I  G  C  H  V  V  N  I  G  A  E  D  L  R  A   161
        TTGGCACTGAACTCTGCTTCTGCCATTGGGTGTCATGTTGTGAACATTGGTGCAGAAGATTTGAGGGCT
        ::::: ::::::::::: :: ::::: ::::: ::::: :: ::::: :: :: :: ::  ::: ::  
        TTGGCTCTGAACTCTGCCTCAGCCATCGGGTGCCATGTGGTCAACATAGGGGCTGAGGACCTGAAGGAG
         L  A  L  N  S  A  S  A  I  G  C  H  V  V  N  I  G  A  E  D  L  K  E
         L  A  L  N  S  A  S  -  I  G

         G  K  P  H  L  V  L  G  L  L  W  Q  I  I  K  I  G  L  F  A  D  I  E   184
        GGAAAACCTCATCTGGTTTTGGGACTGCTTTGGCAGATCATTAAGATCGGTTTGTTCGCTGACATTGAA
        ::::: ::: :::::::  ::::::: :: :::::  :::: ::::: :: ::::: ::::::::::::
        GGAAAGCCTTATCTGGTCCTGGGACTTCTGTGGCAAGTCATCAAGATTGGGTTGTTTGCTGACATTGAA
         G  K  P  Y  L  V  L  G  L  L  W  Q  V  I  K  I  G  L  F  A  D  I  E
                                                     peptide #3 -> A  D  I  E

         L  S  R  N  E  A  L  A  A  L  L  R  D  G  E  T  L  E  E  L  M  K  L   207
        TTAAGCAGGAATGAAGCCTTGGCTGCTTTACTCCGAGATGGTGAGACTTTGGAGGAACTTATGAAATTG
         : ::::: ::::::::  ::  :::: :  :  :::: :::::::   :::::::  : :::::: : 
        CTCAGCAGAAATGAAGCTCTGATTGCTCTTTTGAGAGAAGGTGAGAGCCTGGAGGATTTGATGAAACTC
```

TABLE 2-continued

```
 L  S  R  N  E  A  L  I  A  L  L  R  E  G  E  S  L  E  D  L  M  K  L
 L
 S  P  E  E  L  L  L  R  W  A  N  F  H  L  E  N  S  G  W  Q  K  I  N     230
TCTCCAGAAGAGCTTCTGCTTAGATGGGCAAACTTTCATTTGGAAAACTCGGGCTGGCAAAAAATTAAC
:: :: ::::::::  :::: :: ::::: :: :  ::  :::::::    :::::  : ::::::  :
TCCCCTGAAGAGCTCTTGCTGAGGTGGGCTAATTACCACCTGGAAAATGCAGGCTGCAACAAAATTGGC
 S  P  E  E  L  L  L  R  W  A  N  Y  H  L  E  N  A  G  C  N  K  I  G

 N  F  S  A  D  I  K  D  S  K  A  Y  F  H  L  L  N  Q  I  A  P  K  G     253
AACTTTAGTGCTGACATCAAGGATTCCAAAGCCTATTTCCATCTTCTCAATCAAATCGCACCAAAAGGA
::::: ::: ::::::::::::: :: ::::: :::: ::: :: ::  : ::  : :: :::::::::
AACTTCAGTACTGACATCAAGGACTCAAAAGCTTATTACCACCTGCTTGAGCAGGTGGCTCCAAAAGGA
 N  F  S  T  D  I  K  D  S  K  A  Y  Y  H  L  L  E  Q  V  A  P  K  G

 Q  K  E  G  E  P  R  I  D  I  N  M  S  G  F  N  E  T  D  D  L  K  R     276
CAAAAGGAAGGTGAACCACGGATAGATATTAACATGTCAGGTTTCAATGAAACAGATGATTTGAAGAGA
 :  : :::::::  ::     : : :::: :::::::::: :    :: :  :::::  :  :::: 
GATGAAGAAGGTGTTCCTGCTGTTGTTATTGACATGTCAGGACTGCGGGAGAAGGATGACATCCAGAGG
 D  E  E  G  V  P  A  V  V  I  D  M  S  G  L  R  E  K  D  D  I  Q  R

 A  E  S  M  L  Q  Q  A  D  K  L  G  C  R  Q  F  V  T  P  A  D  V  V     299
GCTGAGAGTATGCTTCAACAAGCAGATAAATTAGGTTGCAGACAGTTTGTTACCCCTGCTGATGTTGTC
:: ::  : ::::: :: :: :: :: :   : :: ::: : :::::::: ::  :  : :::::::::
GCAGAATGCATGCTGCAGCAGGCGGAGAGGCTGGGCTGCCGCCAGTTTGTCACAGCCACAGATGTTGTC
 A  E  C  M  L  Q  Q  A  E  R  L  G  C  R  Q  F  V  T  A  T  D  V  V

 S  G  N  P  K  L  N  L  A  F  V  A  N  L  F  N  K  Y  P  A  L  T  K     322
AGTGGAAACCCCAAACTCAACTTAGCTTTCGTGGCTAACCTGTTTAATAAATACCCAGCACTAACTAAG
 : :: ::::::::  : ::::: :::::  : :: ::::: ::::: : :::::: :: ::    :: 
CGAGGGAACCCCAAGTTGAACTTGGCTTTTATTGCCAACCTCTTTAACAGATACCCTGCCCTGCACAAA
 R  G  N  P  K  L  N  L  A  F  I  A  N  L  F  N  R  Y  P  A  L  H  K

 P  E  N  Q  D  I  D  W  T  L  L  E  G  E  T  R  E  E  R  T  F  R  N     345
CCAGAGAACCAGGATATTGACTGGACTCTATTAGAAGGAGAAACTCGTGAAGAAAGAACCTTCCGTAAC
:::::::::::::: :::::::::       : ::::: :: ::  : :::::  : :: ::  : :::
CCAGAGAACCAGGACATTGACTGGGGGGCTCTTGAAGGTGAGACGAGAGAAGAGCGGACATTTAGGAAC
 P  E  N  Q  D  I  D  W  G  A  L  E  G  E  T  R  E  E  R  T  F  R  N

 W  M  N  S  L  G  V  N  P  H  V  N  H  L  Y  A  D  L  Q  D  A  L  V     368
TGGATGAACTCTCTTGGTGTCAATCCTCACGTAAACCATCTCTATGCTGACCTGCAAGATGCCCTGGTA
::::::::::: :: ::::: :: ::::  :: :: ::: : ::  ::::: :  ::::::::::::: 
TGGATGAACTCCCTGGGTGTTAACCCTCGAGTCAATCATTTGTACAGTGACTTATCAGATGCCCTGGTC
 W  M  N  S  L  G  V  N  P  R  V  N  H  L  Y  S  D  L  S  D  A  L  V
                 peptide #4 -> V  N  -  L  Y  -  D  L
 I  L  Q  L  Y  E  R  I  K  V  P  V  D  W  S  K  V  N  K  P  P  Y  P     391
ATCTTACAGTTATATGAACGAATTAAAGTTCCTGTTGACTGGAGTAAGGTTAATAAACCTCCATACCCG
::::: ::: : ::::::   :: :::::::::::::::::::  :  :: :: ::::: :::::::: 
ATCTTCCAGCTCTATGAAAAGATCAAAGTTCCTGTTGACTGGAACAGAGTAAACAAACCGCCATACCCC
 I  F  Q  L  Y  E  K  I  K  V  P  V  D  W  N  R  V  N  K  P  P  Y  P

 K  L  G  A  N  M  K  K  L  E  N  C  N  Y  A  V  E  L  G  K  H  P  A     414
AAACTGGGAGCCAACATGAAAAAGCTAGAAAACTGCAACTATGCTGTTGAATTAGGGAAGCATCCTGCT
:::::::::: ::: ::::: ::::: :: :: :: ::::: :: :: ::::: :::::: :::  ::
```

TABLE 2-continued

```
               AAACTGGGAGGCAATATGAAGAAGCTTGAGAATTGTAACTACGCGGTAGAATTGGGGAAGAATCAAGCT
                K  L  G  G  N  M  K  K  L  E  N  C  N  Y  A  V  E  L  G  K  N  Q  A

                K  F  S  L  V  G  I  G  G  Q  D  L  N  D  G  N  Q  T  L  T  L  A  L   437
               AAATTCTCCCTGGTTGGCATTGGAGGGCAAGACCTGAATGATGGGAACCAAACCCTGACTTTAGCTTTA
               :: ::::::::::::::::: :: :: ::::: :: :::: :::: :: :: ::  : :: :: :: 
               AAGTTCTCCCTGGTTGGCATCGGTGGACAAGATCTCAATGAAGGAAACCGCACTCTCACACTGGCCTTG
                K  F  S  L  V  G  I  G  G  Q  D  L  N  E  G  N  R  T  L  T  L  A  L
peptide #5 ->      F  S  L  V  G  I  G  G  Q  D  L  N
                V  W  Q  L  M  R  R  Y  T  L  N  V  L  E  D  L  G  D  G  Q  K  A  N   460
               GTCTGGCAGCTGATGAGAAGATATACCCTCAATGTCCTGGAAGATCTTGGAGATGGTCAGAAAGCCAAT
                : :::::::: :::::::: ::::: :: ::: :::: ::::::  :::: : ::: :::: :: : ::::
               ATTTGGCAGCTAATGAGAAGGTATACACTGAATATCCTCGAAGAAATTGGTGGTGGCCAGAAGGTCAAT
                I  W  Q  L  M  R  R  Y  T  L  N  I  L  E  E  I  G  G  G  Q  K  V  N
                                                                 peptide #6 -> V  N
                D  D  I  I  V  N  W  V  N  R  T  L  S  E  A  G  K  S  T  S  I  Q  S   483
               GACGACATCATTGTGAACTGGGTGAACAGAACGTTGAGTGAAGCTGGAAAATCAACTTCCATTCAGAGT
               :: ::::: ::::: :::::::::::   ::: ::::: :::::: :  :::    : :::::    :::
               GATGACATTATTGTCAACTGGGTGAATGAAACATTGAGGGAAGCAGAGAAAAGTTCATCCATCTCTAGT
                D  D  I  I  V  N  W  V  N  E  T  L  R  E  A  E  K  S  S  S  I  S  S
                D  D  I  I  V  N  W  V  N  E
                F  K  D  K  T  I  S  S  S  L  A  V  V  D  L  I  D  A  I  Q  P  G  C   506
               TTTAAGGACAAGACGATCAGCTCCAGTTTGGCAGTTGTGGATTTAATTGATGCCATCCAGCCAGGCTGT
               :: ::::::  :: ::: ::  : ::: :: : ::: ::::  : :: ::::::::::: ::::: :  
               TTCAAGGACCCGAAGATTAGTACAAGTCTGCCTGTTCTGGACCTCATCGATGCCATCCAACCAGGTTCC
                F  K  D  P  K  I  S  T  S  L  P  V  L  D  L  I  D  A  T  Q  P  G  S
                 peptide #7 -> I  S  T  S  L  –  V  L  D  L  I  D
                I  N  Y  D  L  V  K  S  G  N  L  T  E  D  D  K  H  N  N  A  K  Y  A   529
               ATAAACTATGACCTTGTGAAGAGTGGCAATCTAACAGAAGATGACAAGCACAATAATGCCAAGTATGCA
               :: ::::::::::::: ::::::  :  ::::: :  :: ::::: :: : ::: ::::: :: ::::: 
               ATTAACTATGACCTTCTGAAGACAGAAAATCTGAATGATGATGAGAAACTCAACAATGCAAAATATGCC
                I  N  Y  D  L  L  K  T  E  N  L  N  D  D  E  K  L  N  N  A  K  Y  A

                V  S  M  A  R  R  I  G  A  R  V  Y  A  L  P  E  D  L  V  E  V  K  P   552
               GTGTCAATGGCTAGAAGAATCGGAGCCAGAGTGTATGCTCTCCCTGAAGACCTTGTGGAAGTAAAGCCC
                : :: :::::  ::: ::: ::::: :::::::::::: :: :: ::::::::: :: :::::: :: :::
               ATCTCTATGGCCCGAAAAATTGGAGCAAGAGTGTATGCCCTGCCAGAAGACCTGGTTGAAGTGAACCCC
                I  S  M  A  R  K  I  G  A  P  V  Y  A  L  P  E  D  L  V  E  V  N  P
                                peptide #8 -> V  Y  A  L  P  E  D  L  V  E  V
                K  M  V  M  T  V  F  A  C  L  M  G  R  G  M  K  R  V  .   570
               AAGATGGTCATGACTGTGTTTGCATGTTTGATGGGCAGGGGAATGAAGAGAGTGTAA
               :: ::::::::::: ::::::::: ::  : ::::: :  ::::::::::: :::: :
               AAAATGGTCATGACCGTGTTTGCCTGCCTCATGGGGAAAGGAATGAAGAGGGTGTGA
                K  M  V  M  T  V  F  A  C  L  M  G  K  G  M  K  R  V  .
```

When the cDNA was sequenced, four of the oligopeptide sequences that had been unambiguously identified by direct amino acid sequence determination were found (Table 2). The four sequences, peptides No. 1, 2, 6 and 7, starting at amino acid residues 85, 132, 458 and 489, respectively, were unambiguously identified. The other four sequences (peptides No. 3, 4, 5 and 8) were deduced from mixed sequences using the completed cDNA sequence.

There were, however, six differences between the protein sequence (residues 85, 94, 132, 459, 491, and 496) derived from the lymphocyte plastin protein sequence and the reverse-translated cDNA sequence of the cDNA isolated from transformed fibroblasts (Table 2B). These differences indicated that a different but closely related cDNA had been cloned. To identify the protein translation product of the cloned P4 cDNA, the entire 4.3 kb cDNA insert was used to select for mRNAs by hybridization from PolyA+RNA of HuT-14. Then subsequently, the selected mRNAs were translated in vitro.

Total cellular RNA was prepared by the guanidine hydrochloride method, as described previously (Gunning et al, supra). PolyA+RNA was prepared by oligo(dT)-cellulose chromatography (Aviv et al, *Proc. Natl. Acad. Sci. USA* (1972) 69:1408–1412). The purified cDNA fragment was bound to nitrocellulose paper essentially as described by Parnes et al, *Proc. Natl. Acad. Sci. USA* (1981) 78:2253–2257, except that the DNA solution was not subjected to boiling and was added to nitrocellulose paper with the aid of a Minifold (Schleicher & Schuell, Inc., Kenne, N.H.). Hybridization to mRNA and elution of hybridized mRNA were done as described by Maniatis et al, *Molecular Cloning, a Laboratory Manual*, Cold Spring Harbor Lab., Cold Spring Harbor, N.Y. (1982), except that tRNA was not included in the hybridization solution or during the elution of mRNA. The eluted mRNA was precipitated in the presence of calf liver tRNA (15 Mg/ml) in 70% ethanol. The mRNA was suspended in water and subjected to in vitro translation. All in vitro translation experiments were carried out in a rabbit reticulocyte system purchased from New England Nuclear Corp. (Boston, Mass.). The translated products were then electrophoresed in a two-dimensional polyacrylamide gel and visualized by autoradiography as described previously (Lin et al, supra). The method of 2-D gel electrophoresis and translation of mRNAs selected by hybridization to cDNAs has been described previously (Lin et al, supra). The samples in each gel were as follows.

A. CEM T-lymphoblastoid total cell (ATCC No. CCL119) unfractionated proteins stained with silver (Merril et al, *Electrophoresis* (1982) 3:17–23);
B. KD untransformed human fibroblasts (Leavitt et al (1986) supra), total cell unfractionated proteins labeled with [$^{35}$S] methionine (Leavitt et al, *J. Biol. Chem.* (1980a) 255:1650–1661);
C. HuT-12 transformed human fibroblasts (Leavitt et al (1986), supra), prepared as in B;
D. HuT-14 transformed human fibroblasts 25 (Leavitt et al (1986), supra), prepared as in B;
E. normal human monocyte total unfractionated proteins labeled with [$^{35}$S] methionine (Goldstein et al (1985b) supra);
F. in vitro translated [$^{35}$S] methionine 30 labeled polypeptides of total polyA+ mRNA isolated from HuT-14 transformed fibroblasts (Lin et al, supra)
G. in vitro translated polypeptides of polyA+ mRNA from HuT-14 cells used in F and selected by hybridization to the p4 cDNA;
H. in vitro translated polypeptides of polyA+ mRNA from HuT-14 cells used in F and selected by hybridization to the p107 cDNA;
I. in vitro translation (control) as in H, except that no polyA+mRNA was added to the translation reaction;
J. HuT-12 proteins prepared as in B;
K. HuT-12 proteins prepared as in B, mixed with in vitro translated polypeptides prepared as in H.

Polypeptide X, identified as a 70 kd heat shock response polypeptide in fibroblasts and leukocytes, served as a 2-D gel marker for the more acidic isoform of t-plastin in Gels C and E since it has the same pI and exhibits a slightly higher $M_r$.

The most prominent translation products were two proteins (t-plastins) migrating to more basic isoelectric points than the polypeptide recognized as plastin in the 2-D gel (Gels F, G). These two proteins were abundantly synthesized in both normal and transformed human fibroblasts (Gels B, C), but were undetectable in white blood cells (Gels A and E). As these two proteins were apparently similar to plastin, the 2 kb HindIII fragment of P4 cDNA was used as a probe to rescreen the HuT-14 cDNA library to find related cDNAs.

Several clones were identified by this rescreening. One of them, P107, had the largest insert cDNA (3.7 kb) and was chosen for further examination. In Northern analysis as described above, P107 hybridized to an mRNA of 3.7 kb that were more abundant in CEM lymphocytes, less abundant in transformed HuT-14 fibroblasts, and not detectable in untransformed KD fibroblasts. This was the predicted pattern for plastin mRNA expression in these three cell types (Goldstein et al (1985b), supra). Translation of HuT-14 mRNAs selected by this clone yielded a single polypeptide species that appeared to be identical to plastin in a 2-D gel (Gel H). This in vitro synthesized polypeptide was determined to be electrophoretically identical to l-plastin by mixing the in vitro translation sample in Gel H with labeled unfractionated HuT-12 cellular proteins (Leavitt et al (1986), supra) shown in Gel J. This in vitro translated l-plastin, which was in excess of the endogenous HuT-12 l-plastin, was superimposed upon the endogenous l-plastin following 2-D gel electrophoresis (Gel K). It was therefore concluded that P107 is the true cDNA clone of l-plastin, whereas P4 cDNA encoded a separate polypeptide isoform, t-plastin, closely related to l-plastin.

DNA sequencing of P107 cDNA revealed a coding sequence closely related to that of the initially characterized P4 clone (Table 2). This P107 cDNA sequence contained the amino acid residues determined by protein sequence analysis of plastin isolated from CEM lymphocytes in the positions where discrepancies had existed between protein sequence and P4 cDNA sequence. Each coding sequence encoded a polypeptide of 570 amino acids with molecular weight of 64 kilodaltons. This value (64 kd) is slightly different from the observed $M_r$ value of l-plastin and the two t-plastin polypeptides ($M_r$ 68,000) in a 2-D gel. Post-transitional modification of the polypeptides, such as glycosylation, may account for this discrepancy.

The predicted amino acid composition obtained for plastin by computerized microdensitometry was consistent with the amino acid composition determined from these DNA sequences (Goldstein et al (1985b), supra). That l-plastin is expressed in leukocytes and in transformed fibroblasts (HuT-14) but not in normal fibroblasts is now confirmed because the oligopeptide sequences were derived from l-plastin of lymphocytes and the l-plastin cDNA clone was isolated from transformed HuT-14 fibroblasts. The t-plastin isoforms, on the other hand, are expressed in both normal and transformed fibroblasts, but not in leukocytes.

EXAMPLE 2

Identification of 5' mRNA Sequence

The anchored polymerase chain reaction (PCR) technique (Loh et al, Science 243:217–220 (1989)) was used to amplify the 5' ends of both plastin mRNAs to determine whether there were additional sequences encoding N-terminal amino acids. To synthesize the first cDNA strand, the primer 5'-ACAATCAGGATCATTTT-CCA-3' (1 μG) was annealed to HuT-14 poly(A) RNA (8 μg). cDNA was synthesized by reverse transcription (10-μl reaction volume containing 250 mM KCl and 10 mM Tris hydrochloride (pH 8.3). The reaction mixture was incubated first at 80° C. for 3 min. and then at 49° C. for 45 min). A 20-μl amount of reverse transcription buffer (24 mM Tris hydrochloride (pH 8.3), 16 mM $MgCl_2$, 8 mM dithiothreitol, 0.4 mM each of the four deoxyribonucleotides), 1 μl of ($\alpha$-$^{32}$P)dCTP (3,000 Ci/mmol), and 0.5 82 1 (100 U) of Moloney murine leukemia virus reverse transcriptase (Bethesda Research Laboratories, Inc.) were then added to the 10-μl primer-template mixture.

After 1 hour of incubation at 37° C., the mixture was extracted with phenol-chloroform, and nucleic acids were precipitated twice with ammonium acetate and ethanol. For tailing of cDNAs, the product of first-strand cDNA synthesis was suspended in 40 μl of water and mixed with 5 μl of 10 mM dGTP, 5 μl of tailing buffer (1.4M potassium cacodylate (pH 6.9), 0.3M Tris base, 10 mM $CoCl_2$, 2 mM 2-mercaptoethanol), and 1 μl (15 U) of terminal deoxynucleotide transferase (International Biotechnologies, Inc.).

For PCR amplification, a total of three primers were used in two PCR experiments. One primer, 5'-CTCCAGCTCCCCCCCCCCCCCC-3', was used as the upstream primer in both studies. It contained a SacI site (GAGCTC) for convenient cloning and a dC tail for annealing with the dG tail of the cDNAs. The other two primers were downstream primers. One of them, 5'-GGGGGCCCGCTTTGTTTATCCAGTT-3', was used in the first study and contained an ApaI site (GGGCCC) for convenient cloning and 17 bases that are complementary to both plastin isoform mRNAs starting at codon 128. The other downstream primer, 5'-AAAAGGGCCCATAGGAGTGTTGGGTG-CCAA-3', which was used in the second study, also contained an ApaI site, but the 3'-end sequence of 20 bases was complementary only to l-plastin isoform mRNAs starting at codon 112.

The PCR reactions were set up as follows. Half of the dG-tailed cDNA product (in 87.5 μl of water) was mixed with 10 μl of PCR buffer (100 mM Tris (pH 8.3), 500 mM KCl, 15 mM $MgCl_2$, 0.1% (wt/vol) gelatin), 10 μl of a mixture of 2 mM each of the four deoxyribonucleotides, 1 μg (in 1 μl of water) of each of the upstream and downstream primers, and 0.5 μl (2.5 U) of Taq polymerase (Perkin Elmer-Cetus). This mixture was overlayed with 100 μl of mineral oil and incubated in a Temperature Cycler (Ericomp) for a total of 30 cycles. The cycles consisted of 94° C., 1 min., 45° C. (first five cycles) or 55° C. (last 25 cycles), 1.5 min., and 72° C., 2.5 min. The reaction was finished with an extra 10-min. incubation at 72° C.

For cloning and sequencing of amplification products, the PCR products were either digested with SacI and ApaI or attached to EcoRI linkers after a kinase reaction. Both modified PCR products were then cloned into Bluescript plasmid (Strategene) and sequenced with Sequenase (U.S. Biochemicals).

In the first PCR amplification, an oligonucleotide primer that was homologous to both t- and l-plastin-coding sequences (codons 128 to 133) was used. The product was a single band of DNA in an agarose gel of about 500 base pairs. After SacI-ApaI double digestion, this band was no longer visible. This undigested PCR product was cloned with EcoRI linkers. Three clones were isolated that contained identical sequences which matched 229 bases with the 5' end of the t-plastin cDNA described in Example 1. This PCR-cloned sequence extended for another 265 bases upstream and contained an additional 60 codons (shown in Table 3) of the t-plastin open reading frame heading upstream from the 5' end of the coding sequence for t-plastin described in Example 1. This PCR sequence contained a SacI site at base 206 from its 5' end that could explain the disappearance of the DNA band after a SacI digestion.

In the second PCR amplification study using an oligonucleotide primer specific for l-plastin only (complementary to codons 112 to 118), a single DNA fragment approximately 500 base pairs in length was obtained. The amplified DNA was cloned after SacI-ApaI digestion or attachment of EcoRI linkers. Eleven clones were sequenced, and all exhibited identical sequences except for one that was shorter at its 5' end. The longer sequence overlapped with 183 base pairs of the 5'-end sequence previously reported for l-plastin. The sequence extended for another 308 base pairs upstream, which contained an additional 57 codons (shown in Table 3) of the l-plastin open reading frame heading upstream from the 5' end of the coding sequence for l-plastin described in Example 1.

The l-plastin 5' coding sequence also contained a SacI site at position 278. Therefore, the larger PCR clones that were obtained after SacI-ApaI double digestion were in fact cloned from partially digested PCR fragments. The additional sequences for both l- and t-plastin are shown below in Table 3.

TABLE 3

```
T-                                               AAAGATTCCGAGGTGCAGAAGT
                                                              : : : : :
L-  ACTTCCTGCCTTGTGACCACACACCCAGGCTTGACAAAGCTGTTCTGCAGATCAGAAAGAAGG

T-  TGTCTGAGTGGGTTGGTCGGCGGCAGTCGGGCCAGACCCAGGACTCTGCGACTTTACATCTTT
     ::    :    :    : :    :    :: :::        ::    ::  :   :  ::
L-  GGTTCCTGGTCATACACCAGTACTACCAAGGACAGCTTTTTTCCTGCAAGATCTGTTACCTAA
```

TABLE 3-continued

```
      -3 -2 -1
       M  D  E  M  A  T  T  Q  I  S  K  D  E  L  D  E  L  K  E  A      17
T-  AAATGGATGAGATGGCTACCACTCAGATTTCCAAAGATGAGCTTGATGAACTCAAAGAGGCCT
    :     :  : ::::: :         : ::: : :: ::  :    :: :::: ::: :: :
L-  AGCAATAAAAAATGGCCAGAGGATCAGTGTCCGATGAGGAAATGATGGAGCTCAGAGAAGCTT
                M  A  R  G  S  V  S  D  E  E  M  M  E  L  R  E  A

    F  A  K  V  D  L  N  S  N  G  F  I  C  D  Y  E  L  H  E  L  F      38
T-  TTGCAAAAGTTGATCTCAACAGCAACGGATTCATTTGTGACTATGAACTTCATGAGCTCTTCA
    :::: :::::::::    :  :::: :::: :::  :   : ::::  :  ::::  : ::::
L-  TTGCCAAAGTTGATACTGATGGCAATGGATACATCAGCTTCAATGAGTTGAATGACTTGTTCA
    F  A  K  V  D  T  D  G  N  G  Y  I  S  F  N  E  L  N  D  L  F

    K  E  A  N  M  P  L  P  G  Y  K  V  R  E  I  I  Q  K  L  M* L      59
T-  AGGAAGCTAATATGCCATTACCAGGATATAAAGTGAGAGAAATTATTCAGAAACTCATGCTGG
    :::  :::    :::: :: :: :: :::: :::  :::::::::   : :: :: :::
L-  AGGCTGCTTGCTTGCCTTTGCCTGGGTATAGAGTACGAGAAATTACAGAAAACCTGATGGCTA
    K  A  A  C  L  P  L  P  G  Y  R  V  R  E  I  T  E  N  L  M  A

    D  G  D  R  N  K  D  G  K  I  S  F  D  E  F  V  Y  I  F  Q  E      80
T-  ATGGTGACAGGAATAAAGATGGGAAAATAAGTTTTGACGAATTTGTTTATATTTTTCAAGAGG
      :::::   : :  ::::::: :  :: :: ::::: :: ::: :  : ::::: :: :
L-  CAGGTGATCTGGACCAAGATGGAAGGATCAGCTTTGATGAGTTTATCAAGATTTTCCATGGCC
    T  G  D  L  D  Q  D  G  R  I  S  F  D  E  F  I  K  I  F  H  G

    V  K  S  S  D  I  A  K  T  F  R  K  A  I  N  R  K  E  G  I  C      101
T-  TAAAAAGTAGTGATATTGCCAAGACCTTCCGCAAAGCAATCAACAGGAAAGAAGGTATTTGTG
    ::::::: :  ::: :::::::::::::  : ::::::::::: : ::: ::::: :::::::
L-  TAAAAAGCACAGATGTTGCCAAGACCTTTAGAAAAGCAATCAATAAGAAGGAAGGGATTTGTG
    L  K  S  T  D  V  A  K  T  F  R  K  A  I  N  K  K  E  G  I  C

    A  L  G  G  T  S  E  L  S  S  E  G  T  Q  H  S  Y  S  E  E  E      122
T-  CTCTGGGTGGAACTTCAGAGTTGTCCAGCGAAGGAACACAGCATTCTTACTCAGAGGAAGAAA
    :  : ::::: :::::::::  ::: ::::  :: :: :: :: ::: : :::::::::::::
L-  CAATCGGTGGTACTTCAGAGCAGTCTAGCGTTGGCACCCAACACTCTCATTCAGAGGAAGAAA
    A  I  G  G  T  S  E  Q  S  S  V  G  T  Q  H  S  Y  S  E  E  E

    K  Y  A  F  V  N  W  I  N  K  A  L  E  N  D  P  D  C      140
T-  AATATGCTTTTGTTAACTGGATAAACAAAGCTTTGGAAAATGATCCTGATTGT
    : ::::: ::::: :::::::::::::::::  ::::::::::::::::::::
L-  AGTATGCCTTTGTCAACTGGATAAACAAAGCCCTGGAAAATGATCCTGATTGT
```

EXAMPLE 3

Differential Expression of Plastin Isoforms in Human Cell Transformation

A panel of cultured human cell strains was surveyed with Northern analysis for l-plastin (Blot A) and t-plastin mRNA (Blot B). The methods used were as described for Table 1. Two identical Northern blots, A and B, were hybridized with $P^{32}$-labeled cDNAs of P107, and P4, respectively, to analyze plastin expression. Each blot contained cellular RNAs of the following cell strains.

Lane 1, KD, untransformed human fibroblasts (Leavitt et al, (1986), supra);

Lane 2, R17, untransformed human fibroblasts provided by Thomas Hassel, University of North Carolina;

Lane 3, HuT-12, transformed (neoplastic) human fibroblasts (Leavitt et al, (1986), supra);

Lane 4, HuT-14, transformed, tumorigenic human fibroblasts (Leavitt et al, supra);

Lane 5, HuT-14T, transformed, tumorigenic human fibroblasts (Leavitt et al (1986), supra);

Lane 6, HT1080, human fibrosarcoma (neoplastic) (Goldstein et al, (1985b) supra);

Lane 7, Sarcoma-2, a neoplastic cell line derived from a human lieomyosarcoma and provided by Professor George Milo, Ohio State University, Columbus, Ohio;

Lane 8, HOS, osteosarcoma (Goldstein, et al (1985b) , supra);

Lane 9, CEM, human T-cell leukemia (Aebersold et al (1987b), supra);

Lane 10, AG1484 B-lymphoblast strain from a patient with sporadic bilateral retinoblastoma from the Mutant Human Genetic Cell Repository, Camden, N.J.;

Lane 11, GM1231A retinoblastoma strain from the same patient as AG1484;

Lane 12, Molt-4, T-cell leukemia (Leavitt et al, *J. Biol. Chem.* (1980a) 255:4984–4987);

Lane 13, MG63 osteogenic sarcoma, ATCC No. CRL 1427;

Lane 14, Rat-2, a neoplastic rat cell line, (Leavitt et al, *Nature* (*London*) (1985) 316:840–842);

Lane 15, 3T3, a neoplastic mouse cell line (Leavitt et al (1985), supra).

l-Plastin mRNA and protein were not detected in the diploid, non-neoplastic human fibroblast strains KD and R17, but both strains exhibited t-plastin mRNA and protein (Gel B). Greater than 50 additional diploid human fibroblast strains derived from embryonic lung, skin, foreskin, and gingiva from normal individuals and from patients with various genetic diseases such as Huntington's disease, Bloom's syndrome, Ataxia telangiectasia, and retinoblastoma were examined. Without exception all diploid fibroblast strains exhibited expression of t-plastin in 2-D protein profiles, but not l-plastin. The two transformed fibroblast strains, HuT-12 and HuT-14, derived following mutagenesis of the KD cell culture (Leavitt et al (1980a) supra), exhibited increasing levels of l-plastin polypeptide. The tumorigenic strain HuT-14 expressed more l-plastin mRNA and protein than the three tumorigenic HuT strains (HuT-11, -12, and -13). HuT-14T, an even more tumorigenic substrain of HuT-14 (Leavitt et al, *Cell* (1982) 28:259–2268, Leavitt et al, *J. Mol. Biol.* (1986) 6:2721–2726) was not elevated further in l-plastin expression.

Two cell lines derived from tumor tissue, the human fibrosarcoma cell line (HT1080) and lieomyosarcoma cell line (Sarcoma-2), also expressed l-plastin mRNA transcripts at levels comparable to the HuT strains. These two cell lines were previously shown to express levels of l-plastin protein comparable to the HuT strains (Goldstein et al (1985a), supra). The osteogenic sarcoma cell line HOS synthesized a low level of l-plastin which is barely detectable in 2-D gels (Goldstein et al (1985a), supra), but l-plastin mRNA could not be detected in HOS cells by Northern blot analysis. A second osteogenic sarcoma, MG63, and a retinoblastoma tumor cell line GM 1231A, did not exhibit either the l-plastin mRNA transcript or the l-plastin polypeptide. All of the cell strains listed above expressed relatively constant levels of t-plastin mRNA transcripts and polypeptides except for the retinoblastoma cell line which exhibited no detectable plastin mRNA or protein at all.

l-Plastin expression in additional neoplastic human cell strains derived from ovarian carcinoma, endometrial carcinoma, choriocarcinoma tumors and in vitro transformed keratinocytes was observed. However, some established cell lines derived from an ovarian carcinoma, an adenocarcinoma of the cervix (Hela), a Wilm's tumor and a colon carcinoma do not appear to express l-plastin. In all, 17 independent transformed (neoplastic) human cell lines derived from connective, epithelial and endothelial tissues expressed l-plastin while 12 cell lines derived from other tumor sources did not exhibit l-plastin expression. Three retinoblastoma tumors which have deleted the l-plastin linked ret locus are included in these 12 l-plastin-negative cell lines. One of the retinoblastoma tumor cell lines, GM1231A, is distinguished from all the other cell types in that it did not express either l- or t-plastin.

EXAMPLE 4

Expression of Plastin Isoforms in Human Leukocytes

The three lymphocyte cell lines CEM and Molt-4 (both T-cell leukemias), and AG1484, a transformed B-lymphoblast cell line derived from the same patient as the retinoblastoma GM1231A, synthesized high levels of l-plastin mRNA, but no detectable t-plastin mRNA. Leukemic cell lines such as CEM and normal leukocytes such as peripheral blood leukocytes (Goldstein et al (1985b), supra) and cultured monocytes synthesize the highest levels of l-plastin protein (Goldstein et al (1985b), supra), but no t-plastin protein. More than 20 different lymphoblastoid cell lines were examined, the promyelocytic cell line HL-60 (Anderson et al, Cancer Res. (1985) 45:4995), red blood cells, peripheral blood leukocytes (PBLs) from more than 20 individuals, and subfractions of PBLs including T-cells, NK cells, granulocytes, polymorphonuclear leukocytes, and monocytes (Goldstein et al (1985b), supra). Without exception, all cells of hemopoietic origin except fully differentiated red blood cells exhibited abundant synthesis of l-plastin (Goldstein et al (1985b), supra), and failed to express t-plastin.

EXAMPLE 5

Plastin Genomic Sequences

The genomic representation of both the l- and the t-plastin isoforms was studied in six cell strains including retinoblastoma tumor cells and the B lymphoblast cell line derived from the same retinoblastoma patient. Genomic DNA was prepared by the method described by Maniatis et al, *Cell* (1978) 15:687–701. Ten microgram of each genomic DNA was digested with HindIII to completion, electrophoresed in a 0.7% agarose, and blotted onto nitrocellulose. An eight-fold degenerate 20 nucleotide probe described in Table 1B (Oligo Probe-Antisense) was designed from an l-plastin peptide sequence that exhibited a relatively low degeneracy. This oligonucleotide was synthesized using an ABI solid phase synthesizer. To further minimize degeneracy, preferred codon usage for valine and the weak base pair stabilizing characteristics of inosine (I) in the isoleucine codon (Ohtsuka et al, *J. Biol. Chem.* (1985) 260:2605–2608) were used. The oligonucleotide probe was end labeled with $^{32}P$ and used to screen the HuT-14 cDNA library as previously described (Lin et al, supra) except that hybridization was performed at 42° C. and the hybridized filters were washed at room-temperature with 2x SSC.

Hybridization and washing conditions were identical to those described for Table 1. Two identical genomic blots were hybridized with 32P-labeled cDNAs of P4 and P107, respectively. Each blot contained HindIII-digested genomic DNAs of KD (Lane 1), HuT-12 (Lane 2), HuT-14 (Lane 3), peripheral blood lymphocytes (Lane 4), B-lymphoblast strain AG1484 (Lane 5), and retinoblastoma tumor cell strain GM1231A (Lane 6). Size markers were HindIII fragments of phage DNA. All human cell strains are described above.

The results indicated that the l- and t-plastin genes are located on separate DNA restriction fragments in the human genome, and there was no detectable difference in the restriction digest pattern of the t-plastin gene among all six human cell strains examined. There was also no detectable difference in the restriction digest pattern of the l-plastin gene between diploid human fibroblasts which do not synthesize l-plastin and transformed HuT-12 and HuT-14 human fibroblast strains which synthesize increasing levels of the l-plastin, respectively.

The genomic DNA of peripheral blood leukocytes derived from a healthy human donor had two HindIII fragments of 6.5 kb and 6.0 kb instead of the single band of 6.5 kb found in the other five genomic DNA samples. This individual's peripheral blood leukocytes synthesized the variant (polymorphic) form of the l-plastin (Goldstein et al (1985b, supra) in addition to the normal charge species of l-plastin. The 6.0 kb fragment therefore may be indicative of this variant form of l-plastin.

The genomic DNA of the B lymphoblastoid cell line derived from the retinoblastoma patient exhibited approximately a 50% reduction in hybridization of l-plastin restriction fragments compared to the other five genomic DNA samples including the retinoblastoma tumor from the same patient. The reduced copy number of l-plastin genomic fragments apparent for this cell line was consistent with the observation that the l-plastin gene is linked to the retinoblastoma locus because one of the retinoblastoma alleles has been lost as a result of a large deletion around the retinoblastoma locus on chromosome 13. However, l-plastin genomic sequences did not appear to be reduced to the same extent in the genome of the retinoblastoma of the same patient, ruling out the possibility that the l-plastin gene was tightly linked to the retinoblastoma locus.

In conclusion, the profound degrees of activation or of inactivation observed for both the l-plastin and t-plastin genes in the set of cell strains represented in these six genomic DNA samples does not appear to be caused by gross deletions or rearrangements in the structure of these plastin genes.

EXAMPLE 6

Preparation of Isoform-Specific Polyclonal Antibodies

Rabbit anti-l- and anti-t-plastin antisera were prepared by immunization of New Zealand white rabbits according to the protocol recommended by RIBI ImmunoChem Research, Inc. (Hamilton, Mont.). The rabbits were immunized with 50 μg synthetic peptide (KLH-conjugate) corresponding to either the l- or the t-plastin amino acids 58 through 83 of the sequence shown in Table 3. The synthetic peptides were:

met-ala-thr-gly-asp-leu-asp-gln-asp-gly-arg-ile-ser-phe-asp-glu-phe-ile-lys-ile-phe, for l-plastin; and met-leu-asp-gly-asp-arg-asp-lys-asp-gly-lys-ile-ser-phe-asp-glu-phe-val-tyr-ile-phe for l-plastin.

The rabbits were bled after three booster shots with 50 μg unconjugated synthetic peptide.

One-dimensional gel electrophoresis of bacterially synthesized human l- and t-plastin followed by Western blotting with the rabbit polyclonal anti-(human) l- and t-plastin antibody (1:500 dilution) was performed to evaluate the specificity of the antibodies. Total bacterial proteins of *E. coli* transformed with the full length t- or l-plastin gene were prepared as described in Example 8. Nitrocellulose blots of one-dimensional gels containing total bacterial proteins were prepared as described in Varma et al, (1987) *Exp. Cell Res.* 173:163–173.

The Western blot demonstrated that when rabbits were immunized separately with either of the two oligopeptides, they produced a serum that reacted specifically with the respective immunogen synthetic peptide in indirect microplate ELISA assays (Voller et al, *Manual of Clinical Immunology* (N. R. Rose and H. Friedman, eds., American Society for Microbiology, Wash. D.C., 1980) pp. 345–371 as described in Example 7). In 1-D gel Western blots using total *E. coli* proteins from bacterial strains induced to synthesize either l- or t-plastin, the anti-l-plastin serum reacted specifically with bacterial l-plastin and not bacterial t-plastin. Conversely the anti-t-plastin reacted specifically with bacterial t-plastin and not bacterial l-plastin. Both the anti-l- and the anti-t-plastin antibodies reacted to a diminished degree with a nearly equal amount of purified fimbrin. Both plastin antisera also exhibited cross reactions with other *E. coli* proteins, but these cross-reactions were not affected by the absence of isopropyl-beta-galactoside (IPTG) induction of recombinant human proteins.

EXAMPLE 7

Preparation of Isoform-Specific Monoclonal Antibodies

Mouse anti-l- and anti-t-plastin monoclonal antibodies were prepared by immunization of BalbC mice with 50 μg synthetic peptide (KLH-conjugate) corresponding to either the l- or the t-plastin amino acids 58 through 83 described in Example 6. After two booster shots spleen cells were isolated and fused with myeloma cells as described in Varma et al, *Exp. Cell. Res.* (1987) 173:163–173.

Briefly, four days after the last shot, the spleen was isolated. Spleen cells were fused with mouse myeloma AG 8.543 cells (Dr. Ron Levy of Stanford University) using polyethylene glycol 1200. Hybridoma colonies that arose in HAT medium were screened by an ELISA assay measuring human plastin synthetic peptide specificity of anti-l- and t-plastin mouse monoclonal antibodies. Hybrid cells of HAT-resistant colonies were recloned.

The supernatant culture fluid (100 μl) was tested for antibodies which bound in an indirect microplate ELISA assay to the two synthetic peptides used as immunization antigens. The peptides were immobilized in the bottom of wells of a 96-well plastic microtiter plate. The assay was performed as described by Voller et al, *Manual of Clinical Immunology* p.345–371. A one-hour incubation with monoclonal antibody was followed by a 10-minute incubation with the peroxidase conjugate antibody. The optical density of the peroxidase color reaction was measured at a wavelength of 410 nm.

The assay determined the individual hybridoma clones or sub-clones which secreted the highest levels of anti-plastin antibody.

This assay identified four strains of hybridomas that secreted either an l-plastin-(synthetic peptide) specific antibody (such as strain L211D), a t-plastin-(synthetic peptide) specific antibody (such as strain T33D), an antibody which cross-reacted with both synthetic peptide antigens (such as strain L32F), and a strain that secreted to detectable anti-plastin antibody (such as strain L14B). The l-specific antibody and the cross-reacting antibody were elicited with the l-plastin peptide antigen, and the t-specific antibody was elicited with the t-plastin peptide antigen.

The l- and t-specific monoclonal antibodies were used in a dot blot assay to further assess the relatedness of both human plastin isoforms to chick fimbrin. In this experiment approximately 0.4 μg of purified fimbrin, which showed only a single band or electrophoretic species in 1-D and 2-D gels, was dotted directly onto nitrocellulose and reacted with the mouse plastin isoform specific monoclonal antibodies.

The anti-t-plastin monoclonal antibody (T33D) showed significantly stronger affinity for fimbrin than the anti-l-plastin monoclonal antibody (L211D), which gave a weak but visible reaction over the control monoclonal antibody (L14B). The greater reactivity of the t-plastin specific monoclonal antibody towards fimbrin indicates that at least one t-plastin epitope in conserved in fimbrin.

EXAMPLE 8

Preparation of T- and L-plastin Proteins in *E. coli* t- and l-plastin were produced in *E. coli* bacterial strains transfected with the recombinant plasmid pET-3C (Studier et al, *J. Mol. Biol.* (1986) 189:113–130). The plasmid carried either the full-length coding sequence of human l- or t-plastin prepared by the method described in Example 2.

Following transfection, total *E. coli* proteins were prepared in the presence or absence of IPTG induction of synthesis of the human recombinant plastin gene product as described by Studier et al, *J. Mol. Biol.* (1986)

189:113–130. A Coomassie blue-stained 1-D gel demonstrated that proteins of the two plastin isoforms were synthesized in amounts comparable to the most abundant bacterial structural proteins.

SUMMARY OF EXPERIMENTAL RESULTS

Significance of Plastin Isoforms

The plastin gene family that is described above encodes a truly novel set of at least two related but distinct proteins whose expression distinguished cells of solid tissue from hemopoietic or leukocyte cells. l-plastin is a stable protein that is synthesized constitutively at a very high rate in a majority of subtypes of peripheral blood leukocytes and is one of the 10 or 20 most abundant proteins of these normal leukocyte cells. t-plastin currently defines two equally abundant polypeptide species in fibroblasts, epithelial and endothelial cells that have the same molecular weight as l-plastin, but are slightly more basic.

The divergence of l- and t-plastin is striking because these two proteins, though clearly related, have diverged by 17 percent of their amino acids with the replacements scattered almost randomly throughout the 627 amino acid residues of the plastin sequence. Thirty-three percent of these amino acid exchanges involve charged amino acid replacements with 7 short peptide domains exhibiting significantly greater divergence (see Table 2: residues 1–12 [50%], residues 18–30 [58%], residues 224–230 [57%], residues 258–275 [50%], residues 449–459 [50%], residues 487–496 [50%], and residues 512–523 [58%]). Both the 5′ and 3′ untranslated sequences of these two mRNAs were much more divergent than the sequences within the reading frames.

Finally, the induction of l-plastin expression in human fibroblasts does not appear to correlate with the activation of known oncogenes, since the HuT strains, which lack detectable "activated" oncogenes that will transform 3T3 cells (Cooper et al, *Cancer Res.* (1984) 44:1–10) and HT1080 cells, which have an activated N-ras oncogene (Paterson et al, *Cell* (1987) 51:803–812), abundantly express l-plastin.

The present invention provides novel methods of identifying hemopoietic cells of all types. The invention also provides methods and reagents for determining tissue cells which are in a neoplastic state. The presence of the plastin isoform indicative of the particular states is readily identified using either isoform-specific nucleotide probes or isoform-specific anti-plastin antibodies.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed:

1. A cDNA molecule encoding human plastin having the amino acid sequence specified in Tables 2 and 3.

2. The cDNA molecule of claim 1 wherein said plastin is leukocyte-plastin.

3. The cDNA molecule of claim 1 wherein said plastin is tissue-plastin.

4. The cDNA molecule of claim 1 wherein said cDNA molecule is not more than about 5 kilobase pairs.

5. A probe of at least about 20 nucleotides and not more than about 50 kilobase pairs, said probe comprising a nucleotide sequence including at least about 20 consecutive nucleotides complementary to a cDNA molecule encoding human plastin having the amino acid sequence specified in Tables 2 and 3.

6. A probe of at least about 20 nucleotides and not more than about 50 kilobase pairs, said probe comprising a nucleotide sequence including at least about 20 consecutive nucleotides complementary to a cDNA molecule encoding human plastin having the amino acid sequence specified in Tables 2 and 3, said probe having less than about 60% identity with a DNA sequence encoding the other plastin isoform.

7. The probe of claim 6 wherein said probe is complementary to a DNA sequence encoding the sequence covering amino acids 58 through 82 and/or N-terminal 20 amino acids of said plastin isoform.

8. The probe of claim 6 wherein said probe is a DNA sequence.

9. A peptide of less than about 100 amino acids, said peptide comprising at least about 10 consecutive amino acids of:

(a) MLDGDRNKDGKISFDEFVYI;
(b) MATGDLDQDGRISFDEFIKI;
(c) MDEMATTQISKDELDELKEA; or
(d) MARGSVSDEEMMELREAFAK.

10. A method of determining whether a cell is neoplastic comprising:

determining the presence of leukocyte-plastin and tissue-plastin in said cell, wherein a cell comprising both leukocyte-plastin and tissue-plastin is determined to be neoplastic.

11. The method of claim 10 wherein said determining comprises detecting the presence of tissue-plastin mRNA and leukocyte-plastin mRNA in said cell.

12. The method of claim 10 wherein said determining comprises detecting the presence of leukocyte-plastin and tissue plastin.

13. A method of determining whether a cell is a hemopoietic cell comprising:

determining whether said cell comprises tissue-plastin and leukocyte-plastin.

wherein said cell is determined to be hemopoietic when said cell comprises leukocyte-plastin but not tissue-plastin.

14. A method of determining whether a cell is neoplastic comprising:

(a) combining under hybridizing conditions RNA from said cell with a first probe of at least about 20 nucleotides and not more than about 50 kilobase pairs comprising a nucleotide sequence including at least about 20 consecutive nucleotides complementary to a cDNA molecule encoding human tissue-plastin having the amino acid sequence specified in Tables 2 and 3 or adjacent transcribed non-coding regions, said first probe having less than about 60% identity with a DNA sequence encoding leukocyte-plastin; and (b) combining under hybridizing conditions RNA from said cell with a second probe of at least about 20 nucleotides and not more than about 50 kilobase pairs comprising a nucleotide sequence including at least about 20 consecutive nucleotides complementary to a cDNA molecule encoding human leukocyte-plastin having the amino acid sequence specified in Tables 2 and 3 or adjacent transcribed non-coding regions, said probe having less than about 60% identity with a DNA sequence encoding tissue-plastin;

wherein a cell having RNA which hybridizes with both said probes is determined to be neoplastic.

15. The cDNA molecule of claim 1 wherein said cDNA molecule additionally comprises adjacent transcribed regions of a human plastin gene.

16. The method of claim 14 wherein each of said probes is complementary to a cDNA molecule encoding the sequence covering amino acids 58 through 82 and/or N-terminal 20 amino acids of the plastin isoform specified in Tables 2 and 3.

* * * * *